United States Patent [19]

George

[11] Patent Number: 5,154,609
[45] Date of Patent: Oct. 13, 1992

[54] INSTRUMENT FOR REGISTRATION OF THE DENTAL BITE

[76] Inventor: Peter T. George, 1441 Kapiolani Blvd. Ste. 520, Honolulu, Hi. 96814

[21] Appl. No.: 730,656

[22] Filed: Jul. 16, 1991

[51] Int. Cl.$^5$ .......................... A61C 9/00; A61C 19/00
[52] U.S. Cl. ........................................ 433/68; 433/72; 433/214
[58] Field of Search .................. 433/68, 70, 71, 72, 433/214

[56] References Cited

U.S. PATENT DOCUMENTS

| | | | |
|---|---|---|---|
| 1,076,534 | 10/1913 | Wallen | 433/214 |
| 1,649,664 | 1/1927 | Carter | 433/72 |
| 2,171,695 | 9/1939 | Harper | 433/214 |
| 3,321,832 | 5/1967 | Weisberg | 433/214 |
| 4,439,147 | 3/1984 | Magill et al. | 433/5 |
| 4,602,905 | 7/1986 | O'Keefe, III | 433/41 |

*Primary Examiner*—Gene Mancene
*Assistant Examiner*—Cindy A. Cherichetti
*Attorney, Agent, or Firm*—James Creighton Wray

[57] ABSTRACT

The present invention provides for an apparatus and method for registration of the dental bite of a patient. An impression plate is provided for insertion into the patient's mouth and incorporates an upper incisor engagement means and an extension protruding out of the patient's mouth. An independent lower incisor engagement means is provided with an extension which is complementary to the upper incisor extension, wherein a groove in the lower extension mates with the upper extension which slides freely therein. Protrusion and retrusion of the lower jaw with respect to the upper jaw causes an anterposterior sliding movement of the lower extension with respect to the upper extension. Calibrations are provided on the extensions for measuring the relative movement therebetween. A lock is provided between the extensions to hold the extensions at a given calibration for registering the bite at that calibration.

8 Claims, 2 Drawing Sheets

INSTRUMENT FOR REGISTRATION OF THE DENTAL BITE

BACKGROUND OF THE INVENTION

This invention relates to dentistry, specifically to a unique instrument that will simplify the accurate attachment of models of the upper and lower dental arches on a dental articulator in the same relationship as occurred in the natural dentition.

In the construction of any rigid dental device that contacts both the upper and lower teeth, models of the patient's upper and lower dentition must be positioned on a dental articulator. It is important that they be related to each other in the same relationship as existed in the patient's mouth. Most functional orthodontic appliances, as well as several other oral devices such as the NAPA in U.S. Pat No. 33,442 to George Nov. 20, 1990, are designed to keep the lower jaw forward. Therefore, the models on the articular must be positioned with the lower model forward relative to the upper model.

The most common way of transferring the dental relationship in the mouth to the articulator is with a simple wax bite. The dentist softens a block of wax with heat and inserts it between the patient's upper and lower teeth. The dentist then guides the jaw to the desired position and tells the patient to hold it there while the wax cools and hardens. The models of the patient's upper and lower teeth then can be correctly related to each other by fitting them into the indentations in the wax. The models, with the wax between them, are then attached to the articulator. This is done in a manner that will allow the wax bite to be discarded and still allow the articulator, which simulates jaw movements, to open and close back to the wax bite position.

The relationship of the mandible to the maxilla is determined by the relative positions of the incisal edges of the lower to upper central incisor teeth. The distances between them are measured in three planes in space to determine their vertical, anteroposterior, and transverse relationships.

Three problems face the dentist when attempting to register this mandibular position using the free-hand wax bite technique described above.

1. The dentist must keep in mind where in space those three positions are for each individual patient. Those positions can only be estimates since he has no gauge or stop to let him know when the correct relationship has been reached. The most difficult of those is the anteroposterior. Most often this position is selected relative to the individual patient's ability to protrude the jaw, e.g. three-fourths the distance from the most retruded to the most protruded position of the mandible. Since this ability varies among patients, the dentist must remember where the most retruded and most protruded positions were, then use his judgment as to when the jaw has moved forward three-fourths that distance. The difficulty of this determination is compounded when simultaneously attempting to assure the accuracy of the other two positions.

2. The dentist must be able to communicate to the patient how far and in which direction to move the jaw, and when to stop moving. The verbal instructions must be given precisely and clearly, and they must be interpreted accurately and immediately or the correct positions will be over or undershot.

3. Some patients are poorly coordinated, and their muscular responses are not what they intend. For example, when closely approaching the correct position, they may involuntarily jerk the jaw, rendering the wax bite either unusable or imprecise.

In spite of its difficulties and inaccuracies, the free-hand wax bite technique described above remains the most commonly used method of transferring the jaw relationship as it exists in a patient to an articulator. The reason for this is that heretofore no one has devised an easier method that can properly position the jaw. Several jigs have been introduced to improve the bite registration technique, but all of them have serious shortcomings.

One such jig (U.S. Pat. No. 4,439,147 to Keys and Magill, Apr. 17, 1984) is a single-piece instrument which engages the lingual aspect of the lower incisors by which those teeth can be pulled forward until the instrument contacts the lingual aspect of the upper incisors, at which point the lower teeth are lined up directly under the upper teeth. This is the only relationship of lower to upper dental arches that this jig can produce. However, many oral devices should be constructed with the lower incisors more anterior than the upper incisors.

Another single-piece jig, trademark ExactoBite, attempts to give a greater selection of positions for the lower teeth. This instrument has a notch into which the upper front teeth are keyed and three notches into which the lower teeth may fit. However, with this instrument it is possible to relate the lower incisors in only the following three positions: directly under, approximately four millimeters ahead, and approximately four millimeters behind the upper incisors. Although the notches for the lower teeth on this jig are too far apart to allow precise positioning, they are too close together to allow easy selection when guiding the teeth to the desired bite.

No current method allows the dentist to accurately place and register the protruded position of the jaw, e.g. at precisely three-fourths the distance forward from the most retruded to the most protruded position of the jaw.

Most dentists would desire to use an instrument that would enable them to easily, accurately and reliably relate the lower jaw to the upper jaw in any position from the most posterior to the most anterior along the protrusive path.

SUMMARY OF THE INVENTION

The present invention provides instrument for registration of the dental bite. The instrument has a means for engaging teeth of the mandible, a means for engaging the teeth of the maxilla, a connection between the mandible and maxilla engagement means, and calibrations provided on the connection for measuring relationships between the mandible and the maxilla. The maxilla engagement means incorporates an impression platform integrally formed with an extension, and an upper teeth-retaining means formed on an upper face of the engagement means. The mandible engagement means has a lower teeth retaining means and integral extension. The connection provided between the mandible and maxilla engagement means prescribing linear, anteroposterior movement is allowed. The calibration scale is provided on the extensions for measuring the anteroposterior movement between the extensions.

The impression plate has upper and lower planar surfaces for holding imprint materials, and the shape of the plate approximates the bite of the upper and lower teeth. The extension is integrally formed to the plate to protrude out of the mouth, and the upper teeth engagement is a groove for mating with upper incisors.

Preferably, the retaining groove is an internal block for engaging the back of the upper incisors and an external block for engaging the front of the incisors. The internal block extends upwards from the upper face of the impression plate and the external block extends upwards from the maxilla engagement means extension. The groove for retaining the incisors is prescribed therebetween. The lower teeth-retaining groove also incorporates an interior block for engaging the rear of the lower incisors and an adjacent exterior block, and the groove is prescribed therebetween. The integral lower extension extends proximal the exterior block out of a patient's mouth.

The connection between the upper (maxilla) and lower (mandible) extensions further provides the extensions being mated, longitudinal protrusions, wherein the mating provides a tongue-in-groove relationship for an anteroposteriorly linear relationship.

In a preferred embodiment, the mandible extension incorporates a longitudinal groove for receiving the maxilla extension, allowing the slidable attachment therebetween.

Preferably, a locking mechanism is provided to fix the maxilla extension within the mandible extension groove at a given point along its length. The calibrated scale is spaced indicators on the mandible extension to measure the relationship of the maxilla extension within the groove. These can be marks in the groove, to be measured by the end of the maxilla extension within the groove.

The upper extension can further have a shank integrally formed with the plate and a measuring arm. An attachment means between the arm and the shank allows replacement of the impression plate.

In this embodiment, the shank incorporates a number for notation of the size of the impression plate, wherein different sizes require different numbers.

More specifically, the instrument for registration of a dental bite has an impression plate with two opposite planar surfaces approximating the shape of the bite of the mandible and maxilla. A flattened, hollowed semicircle is prescribed, said semicircle fitting into the mouth with two end portions proximal the molars and the central portion proximal the upper incisors. An integral extension protrudes from the central portion of the plate planarly. The extension is a longitudinal arm having an end proximal the plate and a distal end. An upper incisor-retaining device is provided proximal the junction of the plate and the extension. A lower incisor engagement means and integrally formed lower extension is provided with an upper extension-receiving groove for mating co-linearly with the plate and upper extension assembly. The groove is provided with a calibrated scale for measuring the placement of the upper extension within the groove and a lock is provided between the extensions for holding the extensions non-movably.

The upper extension is basically a two-piece apparatus having the measuring arm end and the plate abutment end. The connection between the ends devices a shank proximal the plate end and a measuring arm proximal the measuring arm end. The connection provides a means for switching plates and varying the sizes thereof.

The incisor-retaining means, both upper and lower, have inner and outer blocks forming a recess therebetween. The blocks are raised formations from the faces of the plate and extensions. The upper incisor-retaining means incorporates an inner block raised on an upper face of the impression plate proximal the connection with the extension and outer block formed on the extension proximal the junction with the plate. The indentation (recess) is provided at the junction between the plate and the extension. A sighting means on the upper incisor outer block is provided for centering the plate and integral extension within the user's mouth. The sighting means can be a marked line on the outer block for sighting between the upper front incisors of the user.

The scale can be spaced calibrations with a central marker point and evenly spaced coded markers on either side of the central marker, wherein measurement of protrusion and retrusion of the maxilla to mandible is provided through the mating of the upper and lower extensions of the registration device. The measuring arm end of the upper extension is measured against the scaled markers within the groove.

A further method for registration of a dental bite describes independently securing the upper and lower incisors and exteriorly mating the securement means with a movable engagement. The allowed movement is in the anteroposterior direction. The engagement means between the upper and lower securement means are calibrated so that relaxed bite, and protruded and retruded anteroposterior movements can be measured to provide the amount of dental overjet of the patient. Locking the engagement between the upper and lower securement means and registering of the bite of the patient at that given calibration provides a new method for registration which is more accurate than previous methods.

Accordingly, the following are objects and advantages of the invention.

1. An instrument whereby dentists can easily, accurately and reliably transfer dental models to a dental articulator in any anteroposterior relationship of the lower to the upper natural dentition 2. Such an instrument which can measure the most retruded and most protruded position of the mandible on a millimeter scale.

3. Such an instrument with notches for the upper and lower incisors which are adjustable anteroposteriorly to any position along the protrusive path of the mandible.

4. Such an instrument with a locking mechanism to secure the anteroposterior relationships of the notches to the precise desired relationship of the upper and lower incisors during the protrusion of the mandible.

5. Such an instrument with a large single notch for the lower incisors, making it easy to locate.

6. Such an instrument which requires a minimum of training for a dentist to use.

These and further and other objects and features of the invention are apparent in the disclosure, which includes the above and ongoing written specification, with the claims and the drawings.

DETAILED DESCRIPTION OF THE DRAWINGS

Figure 1:
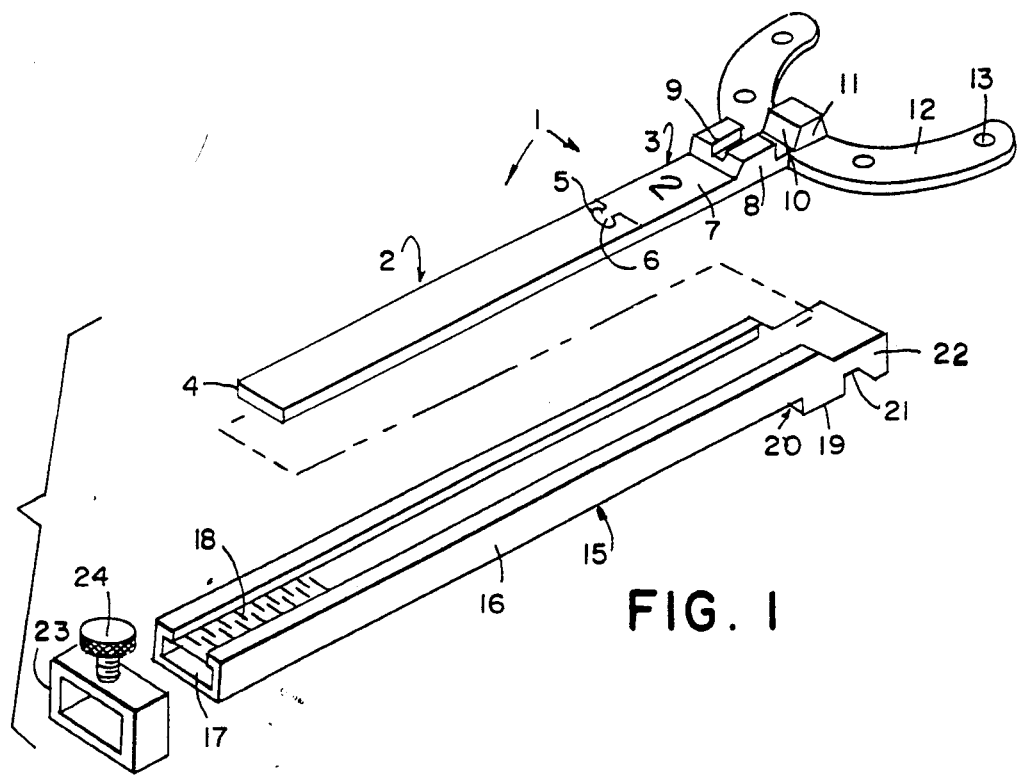
FIG. 1 is an elevated side view of a preferred embodiment of the invention.

FIG. 1 shows a perspective exploded view of the three pieces of the preferred embodiment of the invention. All parts may be made of plastic and/or metal. The upper assembly 1 incorporated the upper platform 3 and a measuring arm 2.

At the internal end of the upper platform is the impression platform 12 with gripper holes 13 to help secure the impression material on the platforms. (In this description the term "internal" refers to inside the mouth or toward the inside of the mouth, and "external" refers to outside the mouth or toward the outside of the mouth.)

The upper teeth indention 10 is formed on the superior side of the upper platform 3 by a notch which separates the upper internal block 11 from the upper external block 8. The latter has a center line 9 to help relate the center of the instrument with the center of the upper teeth. In one embodiment, the upper teeth indention 10 is 4 mm deep from the tops of the upper internal and external blocks. Preferably it is 2 mm at the bottom and 5 mm at the top measured in an external to interal direction. Its external wall rises at 90°, and its internal wall rises at 45°. The thickness of the floor of the upper teeth indention can vary depending upon the amount of vertical distance desired between the upper and lower incisors. As the thickness of this floor increases, the heights of the upper internal and external blocks increase by the same amount so that the depth of the upper teeth indention remain constant, as in a preferred embodiment, at 4 mm.

At the external end of the upper platform 3 is the shank 7 which connects with the measuring arm 2 by its male portion of the snap lock 6. Other suitable connections are within the scope of the invention. The most internal (proximal) end of the measuring arm is connected to the upper platform by its female portion of the snap lock 5. The most external border of the measuring arm 2 is the measurement point 4 which relates to the scale 18 of the lower assembly 15. On the superior surface of the shank 7, a number X may be formed in the plastic which indicates the amount of vertical distance between the upper and lower incisor teeth that will be established by using that upper platform. That distance is determined by the thickness of the floor of the upper teeth indention, plus the thickness of the ceiling of the lower teeth indention 21. However, the lower indention ceiling remains constant at 1 mm.

The fact that the upper platform can be snapped on and off provides several important advantages. It can be interchanged with an identical member while it is sent to the dental laboratory, where it may remain for a day or several weeks. It can also be interchanged with an upper platform that will register a bite with a greater or smaller interincisal vertical distance.

The upper assembly fits within the lower assembly by inserting the measuring point 4 in the internal (proximal) end of the channel 16, as shown by the scored line in FIG. 1. At the internal end of the lower assembly on the inferior side, the lower teeth indention 21 is formed by a notch between the lower internal block 22 and the lower external block 19. Its dimensions and configuration are identical to those of the upper teeth indention 10. However, the thickness of the ceiling of the lower teeth indention does not vary as does the thickness of the floor of the upper teeth indention. It stays constant at a thickness of 1 mm. The lower assembly ends at the external end 17, which incorporates calibration or registration scale 18 within the channel 16.

Figure 5:
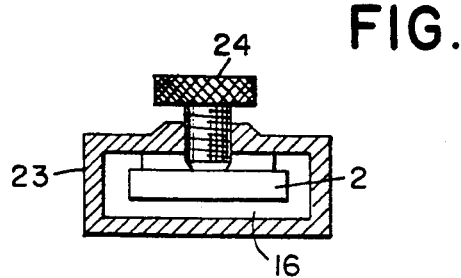
FIG. 5 is an end cutaway showing the tongue-in-groove engagement and preferred lock.

The clamp 23, shown in FIG. 1 as a separate part, is either removably or permanently affixed to or near the middle of the length of the channel 16. The locking screw 24, as shown in FIG. 5, can secure the anteroposterior relationship of the upper to lower assembly by compressing the measuring arm 2 against the floor of the channel 16. Alternatively, the clamp may take the form of other securement devices, such as providing a screw through the side of channel 16 for engaging the side of the arm 2.

Figure 2:
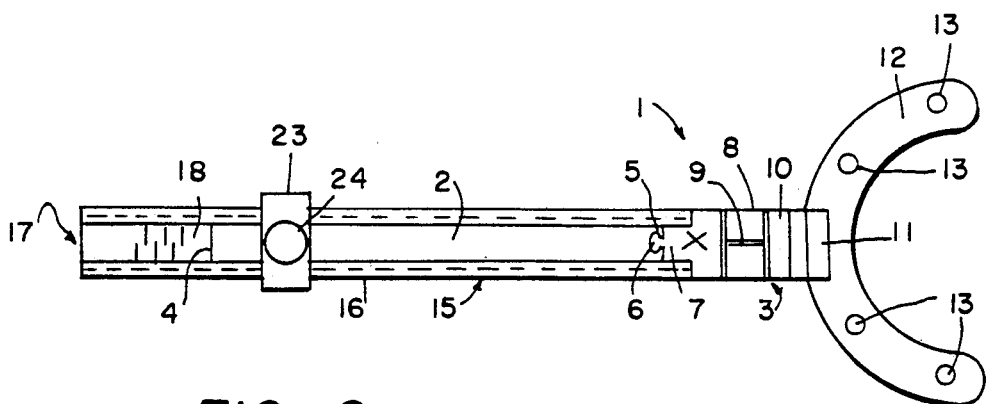
FIG. 2 shows a top view of a preferred embodiment of the invention.

FIG. 2 shows a top view of the preferred embodiment of the invention. At the internal end of the upper platform 3 is the impression platform 12 with gripper holes 13 to secure the impression material on the platforms. At the external end of the impression platform is the upper teeth indention 10 which is formed by a notch which separates the upper internal block 11 from the upper external block 8. The latter has a center line 9 to help relate the center of the instrument with the center of the upper teeth.

At the external end of the upper platform 3 is the shank 7, which connects with the measuring arm 2 by its male portion of the snap lock 6. On the surface of the shank 7, a number X may be formed in the plastic which indicates the amount of vertical distance between the upper and lower incisor teeth that will be established by using that upper platform.

In FIG. 2 the measuring arm 2 is connected to the upper platform 3 by its female portion of the snap lock 5. The connected measuring arm and upper platform are encased in the channel 16 of the lower assembly 15 in which they can freely slide anteroposteriorly. The most external border of the measuring arm is the measurement point 4 which relates to the scale 18 of the lower assembly 15. The most external extent of the lower assembly is the opening 17 of the channel.

At or near the middle of the channel 16 is the clamp 23 which encircles the lower assembly 15 and the encased measuring arm 2. The locking screw 24 can be turned to compress the measuring arm against the floor of the channel, making it immobile.

Figure 3:
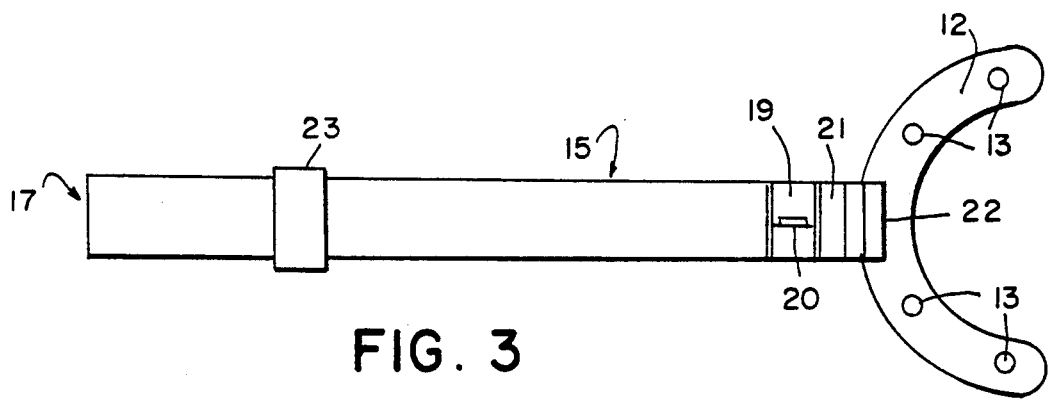
FIG. 3 shows a bottom view of a preferred embodiment of the invention.

FIG. 3 is a bottom view of the preferred embodiment of the invention. At the most internal end of the instrument, the underside of the impression platform 12 with gripper holes 13 to secure the impression material on the platforms can be seen. It is attached to the upper platform 3 which is not visible from this view. At the most internal end of the lower assembly 15 is the lower teeth indention 21, which is formed by a notch which separates the lower internal block 22 from the lower external block 19. The latter has a center line 20 to help relate the center of the instrument with the center of the lower teeth. At or near the middle of the lower assembly 15 is the clamp which encircles it. At the most external end of the lower assembly is the opening 17.

Figure 4:
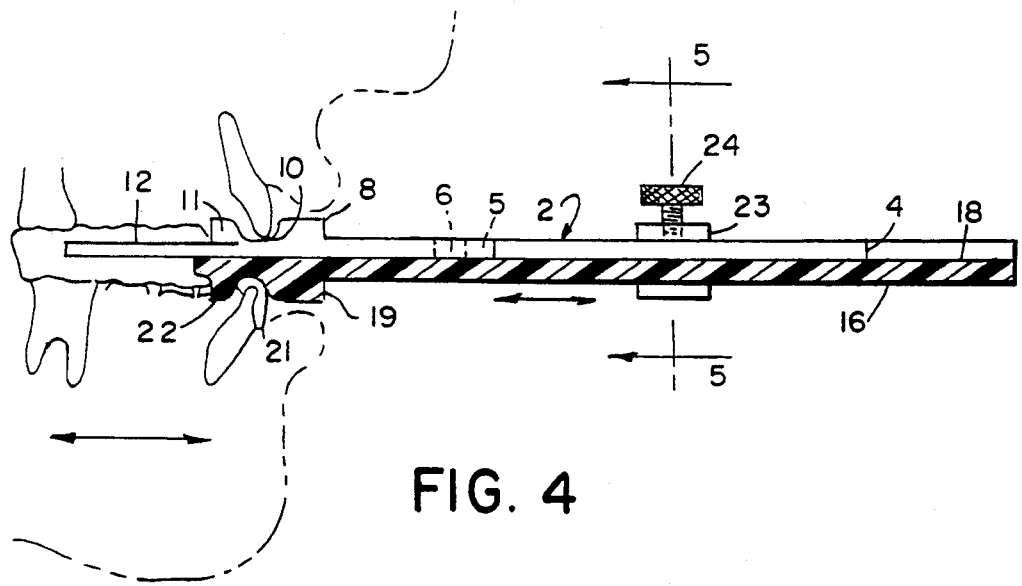
FIG. 4 shows a cutaway side view of the operation of the instrument.

FIG. 4 is a right side sectional view of the invention as it is used in the mouth. The most internal portion of the instrument is the impression platform 12, which in this figure is surrounded by impression material. The upper and lower incisor teeth fit respectively into the upper teeth indention 10 and the lower teeth indention 21. The upper indention is formed by the notch between the upper internal block 11 and the upper external block 8, and the lower indention is formed by the notch between the lower internal block 22 and the lower external block 19. The male portion of snap lock 6 on the external end of the shank 7 of the upper platform 3 interlocks with the female portion of snap lock 5 on the internal end of the measuring arm 2 to hold these two parts of the upper assembly 1 together. Turning the locking screw 24 of the clamp 23 compresses the measuring arm 2 against the floor of the channel 16, thereby securing the anteroposterior relationship of the upper assembly 1 to the lower assembly 15, as in FIG. 5. The external end of the measuring arm is the measuring point 4, which indicates the anteroposterior relationship of upper to lower assembly by its position over the scale 16, which is inscribed in millimeters on the floor of the channel 16. When the lower incisors are directly below the upper incisors as indicated in FIG. 4, the measuring point 4 will be at 0 mm. The millimeter marks on the internal side of 0 mm are negative, and the millimeter marks on the external side of 0 mm are positive.

The bite registration instrument of FIG. 1 will find its greatest utilization in the construction of functional orthodontic appliances, but will be very useful in the construction of any oral device that requires a forward position of the mandible. The instrument is assembled by inserting the measuring point 4 of the measuring arm 2 of the upper assembly 1 into the internal end of the channel 16 of the lower assembly 15. The clamp 23 is not disassembled at any time during normal usage, but is affixed proximal channel 16.

After the instrument is assembled it is taken to the mouth, as shown in FIG. 4, except that there should be no impression material on the impression platform at the initial try-in. The locking screw 24 is loosened so that the upper assembly 1 may slide freely in the channel 16 of the lower assembly 15. The measurement point 4 should be set at or near the 0 mm mark of the scale 18.

The instrument is placed in the mouth so that the upper incisors fit into the upper teeth indention 10, and the patient is instructed to bring his lower incisors up as if to bite end-to-end with the upper incisors. Since the measurement point 4 was placed at the 0 mm mark on the scale 18, the lower incisors will close into the lower teeth indention 21. The dentist will then have the patient move his jaw back and forth to determine the most retruded and protruded positions of the mandible. Unless the patient has a prognathic mandible, the most retruded position will cause the measurement point 4 to travel over the negative numbers of the scale 18. The negative number farthest from 0 mm that the patient can reach will be the number of millimeters his mandible can retrude from an incisal end-to-end position. This is also a new way of recording the amount of dental overjet of a patient.

When the patient protrudes the jaw, the measurement point will travel over positive numbers of the scale. The highest number reached will be the number of millimeters that the patient can protrude his jaw beyond an incisal end-to-end bite. This is also a new way of recording the maximum mandibular protrusion of a patient.

Those two numbers tell the dentist the range of motion of the mandible in an anteroposterior direction. The dentist may then decide to register a bite anywhere long this range. All he need do is set the measurement point 4 at the amount of protrusion or retrusion desired.

He then secures it there by turning the locking screw 24 of the clamp 23.

The tremendous advantage this instrument gives the dentist in being able to accurately register any point along the protrusive path of the mandible becomes apparent when one considers all the different positions of the mandible the various oral devices require. Some require that the device be built to hold the mandible in a position that is a certain percentage of the distance forward from the most retruded to the most protruded position. Some require a position that is the most protrusive possible, less one or more millimeters. Others require that the mandible be registered in an end-to-end position or a millimeter or two ahead or behind. Still others require a position that is a certain number or millimeters ahead of the most retruded position of the mandible. Most of these positions cannot be registered by any existing instrument, and their locations can only be estimated in the free hand technique depending heavily on the skill of the dentist and the cooperation of the patient. Many dentists will use a jig like the ExactoBite or U.S. Pat. No. 4439,147, not because it gives them the ideal position, but because it is a better position than they can obtain free-hand. Some dentists completely avoid working with functional orthodontic appliances or other devices requiring a protrusive bite registration because of their lack of confidence in taking an acceptable registration.

Once this invention becomes available, many dentists who previously did not work with functional orthodontic appliances and other oral devices requiring a protrusive bite registration will include them in their armamentarium. Dentists who have been routinely using these devices will become more discerning about the position at which they want to register the bite. They will be able to notate in the patient's records the exact position of the mandible the device was constructed to maintain. This will provide important clinical feedback for the dentist when evaluating the efficacy of various appliances. Textbooks and dental professors will be able to give more explicit instructions on where to register the mandible for the construction of the various appliances and feel confident that their readers or students will be able to achieve such registrations. It will greatly improve the communication among dentists and dental students in describing or discussing bite registrations.

After the dentist has secured the instrument in the exact position he wants, he will attach impression material on impression platform 12, and take the instrument back to the mouth. He will seat the lower teeth indention 21 over the lower incisors as shown in FIG. 4, and he will instruct the patient to bring the mandible up to allow the upper incisors to bite into the upper teeth indention 10. If the patient is not well coordinated and has difficulty biting directly into the indention, he may be instructed to bite on the upper external block then slide the mandible forward until the upper incisors slip off the internal end of the external block and contact the bottom of the indention. It is easier for the patient to bite on the external block rather than the internal block since less protrusion of the mandible is required to find it. Also it is preferable to bite first on the external block since it has a 90° drop to the indention, whereas the drop-off from the internal block to the indention is 45°. A vertical bite into the impression material provides a more accurate impression than a diagonal slide.

As the patient is bringing the mandible up to position the upper incisors into the upper teeth indention, the patient should be holding a mirror so that he may be able to center the instrument transversely by observing the center line 9 relative to the midline of the upper incisors.

This instrument will allow the use of several different impression materials. Wax may be warmed and folded in layers over both right and left impression platforms 12, or the wax may be wrapped individually around each side of the platform. Sufficient wax is placed around the impression platform so that, when the patient closes into the instrument as described above, the upper and lower posterior teeth will make indentations in the wax. After the wax hardens and is removed from the mouth, the indentations can be used to key the teeth of the patient's dental models to the same relationship as the natural dentition at the time of the bite into the wax.

Silicone impression material, before a hardener is added, has the consistency of putty. It can also be used with this instrument. This material can be molded into a sausage shape then impaled into the right and left arms of the impression platform. The bite registration is then taken as described above.

Vinyl Polysiloxane impression material may be used for patients with very poor coordination who may not be able to find the correct bite before the impression material hardens. This material may be injected between the impression platforms and the posterior teeth. With this material the dentist can take as much time as necessary to properly seat the instrument, then inject the material while the patient simply maintains a biting posture which is stabilized by the instrument.

Other suitable materials are readily used with this invention.

After the impression material has hardened and the instrument is removed from the mouth, the upper platform 3 is pulled out of the channel 16 and is separated from the measuring arm at the snap lock 5, 6. The upper platform with the indented impression material around the impression platform is sent to the dental laboratory, along with the models of the patient's teeth.

The lower assembly 15 and the measuring arm 2 are sterilized, and a new or a sterilized used upper platform may replace the one that was sent to the laboratory. Since some appliances require registration with greater vertical distance between the upper and lower incisors, upper platforms can be manufactured with the floor of the upper teeth indention 10 at varying thicknesses. The thickness of the floor of the upper teeth indention plus the thickness of the ceiling of the lower teeth indention 21 determine the amount of vertical distance between the upper and lower incisors. The floor of the upper indention could be made, for example, in thicknesses of 1 mm, 3 mm, 5 mm and 7 mm. Those amounts, plus the 1 mm for the thickness of the ceiling of the lower teeth indention, are marked on the shank 7.

While the invention has been described with reference to specific embodiments, modifications and variations of the invention may be constructed without departing from the scope of the invention, which is defined in the following claims.

I claim:

1. An instrument for registration of the dental bite, comprising a mandible engagement means for engaging teeth of the mandible, a maxilla engagement means for engaging the teeth of the maxilla, connection means between the mandible and the maxilla engagement means for slidably engaging the maxilla engagement means in the mandible engagement means, and calibration provided on the connection for measuring relationships between the mandible and the maxilla, further comprising the maxilla engagement means incorporating an impression platform integrally formed with an extension, and an upper teeth-retaining means formed on an upper face of the engagement means; the mandible engagement means comprising a lower teeth retaining means and integral extension; connection provided between the mandible and maxilla engagement means provided between the respective extensions wherein linear, anteroposterior movement between the engagement means is allowed; and the calibration scale provided on the extension for measuring the lateral movement between the extensions, further comprising the impression platform having upper and lower planar surfaces for holding imprint materials, wherein the shape of the plate approximates the bite of the upper and lower teeth; the extension integrally formed to the plate to protrude out of the mouth; the upper teeth engagement being a groove for mating with upper incisors, further comprising an internal block for engaging the back of the upper incisors and an external block for engaging the front of the incisors, said internal block extending upwards from the upper face of the impression plate and the external block extending upwards from the maxilla engagement means extension; the groove for retaining the incisors prescribed therebetween.

2. An instrument for registration of a dental bite, comprising an impression plate having two opposite planar surfaces approximating the shape of the bite of the mandible and maxilla, wherein a flattened, hollowed semicircle is prescribed, said semicircle fitting into the mouth with two end portions proximal the molars and a central portion proximal the upper incisors; an integral extension protruding from the central portion of the plate planarly, the extension being a longitudinal arm having an end proximal the plate and a distal end; an upper incisor-retaining device provided proximal the junction of the plate and the extension; a lower incisor engagement means and integrally formed lower extension provided with an upper extension-receiving groove for mating co-linearly with the plate and extension assembly; the groove provided with a calibrated scale for measuring the placement of the upper extension within the groove and a lock provided between the extensions for holding the extensions non-movably.

3. The registration instrument of claim 2, further comprising a two-piece apparatus having the measuring arm end and the plate abutment end, a connection means between the ends prescribing a shank proximal the plate end and a measuring arm proximal the measuring arm end, said connection means providing a means for switching plates and varying the sizes thereof.

4. The registration instrument of claim 3, further comprising spaced calibrations having a central marker point and evenly spaced coded markers on either side of the central marker.

5. The registration instrument of claim 4, further comprising the measurement of protrusion and retrusion of the maxilla to mandible provided through the mating of the upper and lower extensions of the registration device, wherein the measuring arm end of the upper extension is measured against the scaled markers.

6. The registration instrument of claim 2, further comprising inner and outer blocks forming a recess therebetween, said blocks being raised formations; upper incisor-retaining means incorporating an inner block raised on an upper face of the impression plate proximal the connection with the extension and outer block formed on the extension proximal the junction with the plate, the indentation provided at the junction between the plate and the extension.

7. The registration instrument of claim 6, further comprising a sighting means on the upper incisor outer block for centering the plate and integral extension within the user's mouth.

8. The registration instrument of claim 7, comprising a marked line on the outer block for sighting between the upper front incisors of the user.

* * * * *